(12) United States Patent
Wang et al.

(10) Patent No.: US 10,870,869 B2
(45) Date of Patent: Dec. 22, 2020

(54) ENZYMATIC METHOD FOR PREPARING GLYCERYL BUTYRATE

(71) Applicant: SOUTH CHINA UNIVERSITY OF TECHNOLOGY, Guangzhou (CN)

(72) Inventors: Yonghua Wang, Guangzhou (CN); Weifei Wang, Guangzhou (CN); Bo Yang, Guangzhou (CN); Dongming Lan, Guangzhou (CN); Fanghua Wang, Guangzhou (CN); Xuehui Li, Guangzhou (CN); Dongqi Zhu, Guangzhou (CN); Daoming Li, Guangzhou (CN); Zhigang Li, Guangzhou (CN); Huayong Chen, Guangzhou (CN)

(73) Assignee: SOUTH CHINA UNIVERSITY OF TECHNOLOGY, Guangzhou (CN)

( * ) Notice: Subject to any disclaimer, the term of this patent is extended or adjusted under 35 U.S.C. 154(b) by 0 days.

(21) Appl. No.: 16/348,890

(22) PCT Filed: Nov. 8, 2017

(86) PCT No.: PCT/CN2017/109920
§ 371 (c)(1),
(2) Date: May 10, 2019

(87) PCT Pub. No.: WO2018/086529
PCT Pub. Date: May 17, 2018

(65) Prior Publication Data
US 2019/0276861 A1    Sep. 12, 2019

(30) Foreign Application Priority Data

Nov. 11, 2016 (CN) .......................... 2016 1 0994446

(51) Int. Cl.
*C12N 9/20* (2006.01)
*C12P 7/64* (2006.01)

(52) U.S. Cl.
CPC .............. *C12P 7/6454* (2013.01); *C12N 9/20* (2013.01); *C12Y 301/01003* (2013.01)

(58) Field of Classification Search
None
See application file for complete search history.

(56) References Cited

PUBLICATIONS

Hend, G. et al., ch 10 in Recent Trends in Biotechnology, Rai, ed. Jodhpur, India 2004, pp. 95-101.*

\* cited by examiner

*Primary Examiner* — Heidi Reese
(74) *Attorney, Agent, or Firm* — JMB Davis Ben-David

(57) ABSTRACT

An enzymatic method for preparing glyceryl butyrate, comprising: (1) carrying out an esterification reaction between n-butyric acid and glycerol using lipase as a catalyst, ethyl acetate and/or ethyl formate as an additive; (2) separating the reaction product, recovering the additive by distillation under reduced pressure to obtain glyceryl butyrate. The invention uses lipase as a catalyst to catalyze the esterification reaction of n-butyric acid and glycerin at normal temperature and normal pressure, reduces the energy consumption of the reaction. Also, the reaction condition is mild, no side reaction happens, and no water-carrying agent is used. In addition, the additive increases the catalytic efficiency of the lipase and the conversion rate of butyric acid.

15 Claims, No Drawings

ENZYMATIC METHOD FOR PREPARING GLYCERYL BUTYRATE

CROSS-REFERENCE TO RELATED APPLICATIONS

This is the U.S. National Stage of International Patent Application No. PCT/CN2017/109920 filed on Nov. 8, 2017, which was published in Chinese under PCT Article 21(2), and which in turn claims the benefit of Chinese Patent Application No. 201610994446.X filed on Nov. 11, 2016.

TECHNICAL FIELD

The invention relates to an enzymatic method for preparing glyceryl butyrate.

BACKGROUND ART

Butyric acid is a short-chain fatty acid found in the gut of humans and animals, which provides energy for the intestinal epithelial cells to promote their growth. As a precursor of butyric acid, glyceryl butyrate has been widely used in the fields of medical treatment and feed. Butyric acid cannot be decomposed by gastric juice, and would slowly release butyric acid and glycerol under the application of pancreatic lipase. Butyric acid is a product of microbial fermentation of carbohydrates in the rumen of ruminants and omnivorous animals. In recent years, it has been found that butyric acid also has a strong bactericidal effect. Compared with other short-chain fatty acids, butyric acid has an optimal bactericidal activity when it is not decomposed, and it is considered as a potential substitute for antibiotics. Because of the liquid form and volatility of butyric acid, as well as the smelly odor, it is not easy to use directly in feed or food. As a precursor of butyric acid, glyceryl butyrate is easy to use, safe, non-toxic without any side-effect, and has no odor, which solves the problem of butyric acid that volatile liquid is difficult to add, and the odor is smelly. It is also a good nutritional additive which promotes the health of livestock and poultry intestines, improves the immunity, promotes the digestion and absorption of nutrients, and improves the fertility of animals.

Glyceryl butyrate has great potential in the field of animal feed, and many studies have been done on the synthesis of glyceryl butyrate. CN102090517A discloses a process for preparing glyceryl mono-dibutyrate by using butyric acid and glycerin as reactants, carbon tetrachloride as water-carrying agent and phosphoric acid as catalyst; after recovering carbon tetrachloride, phosphoric acid is washed away by saturated saline solution having a pH of 10. CN 102850215A discloses a process for preparing glyceryl butyrate by using toluene as a water-carrying agent and solid acid as a catalyst to catalyze the esterification of n-butyric acid and glycerol; after the reaction is completed, the catalyst is separated by filtration, the water-carrying agent is distilled under reduced pressure for recovery, and then glyceryl butyrate is obtained. Since the water-carrying agent is normally toluene or carbon tetrachloride, the resulted waste water is difficult to treat; therefore, production processes without a water-carrying agent have been developed. CN 104045556A discloses a method for preparing glyceryl tributyrate, which comprises reacting glycerin and butyryl chloride with an organic base as an acid binding agent to obtain a mixture containing glyceryl tributyrate, then extracting the glyceryl tributyrate containing mixture with water, collecting the organic phase, evaporating the solvent in the organic phase under reduced pressure to obtain glyceryl tributyrate. In CN103012137B, p-toluenesulfonic acid is used as a catalyst, and water produced by the esterification reaction is removed by nitrogen gas, and then the reaction product is repeatedly washed with a dilute alkali solution to obtain a crude product of glyceryl butyrate. In CN104086422B, a sulfonic acid mesoporous molecular sieve and ZSM-5 acid zeolites are used to catalyze the esterification of butyric acid and glycerin, while butyric anhydride is added dropwise so as to obtain glyceryl butyrate without water-carrying agent.

In summary, the prior synthesis process of glyceryl butyrate generally uses a chemical catalyst such as acid or base to carry out esterification reaction at a high temperature. The process consumes high energy, and requires complicated procedure to remove the catalyst from the product. Glyceryl butyrate is generally used as a functional nutritional supplement for animal feed. Therefore, the development of an efficient and environmentally friendly bio-enzymatic synthesis process is more conducive to the promotion of glyceryl butyrate in the field of functional feed additives. The enzymatic synthesis of glyceride has attracted great interest, and the enzymatic synthesis of many fatty acids (such as polyunsaturated fatty acids) has been industrialized. However, butyric acid is a short-chain fatty acid which has good mutual solubility with water and glycerin, and has low boiling point and strong volatility, which has great difference in physical and chemical properties with medium-long-chain fatty acids with strong hydrophobicity and high boiling point. When glyceryl butyrate is produced by the conventional production process adapted to medium-long-chain glyceride, the catalytic efficiency of lipase is extremely low; and when the esterification reaction reaches equilibrium, the conversion rate of butyric acid is also very low.

SUMMARY OF THE INVENTION

Generally, all of the conventional synthesis processes of glyceryl butyrate use chemical catalysts and toxic agents such as toluene and carbon tetrachloride are required to be used as a water-carrying agent, and the present invention provides a method for preparing glyceryl butyrate by an enzymatic method. The lipase is used as a catalyst, n-butyric acid and glycerol are used as substrates, ethyl acetate and/or ethyl formate are used as reaction assistants, and the esterification reaction is carried out at normal temperature and normal pressure without using a water-carrying agent.

The present invention aims to achieve the above object, and the technical solution is as follows:

An enzymatic method for preparing glyceryl butyrate, comprising:
   (1) carrying out an esterification reaction between n-butyric acid and glycerol using lipase as a catalyst, ethyl acetate and/or ethyl formate as an additive;
   (2) separating the reaction product, recovering the additive by distillation under reduced pressure to obtain glyceryl butyrate.

The molar ratio of the n-butyric acid to the glycerol in step (1) is 3:1-1:3.

The additive in step (1) may be ethyl acetate, ethyl formate or their mixture at any ratio.

The ethyl acetate or methyl acetate is added in an amount of 10%-60% by mass of the n-butyric acid.

The lipase is added in an amount of 0.5%-10% by mass of the n-butyric acid. The lipase in step (1) is selected from at least one of lipase of Rhizopus, Aspergillus, Mucor, bacteria and yeast, and pancreatic lipase. The lipase may also be, but is not limited to, commercialized Lipozyme TL 100L lipase or Lipozyme®CALB lipase.

The esterification reaction is carried out at 20° C.-50° C. with stirring at a speed of 200 rpm or more. The separating in step (2) is preferably natural stratification, then the organic phase is recovered, and ethyl acetate is distilled under reduced pressure to obtain glyceryl butyrate.

Fatty acid is a natural substrate of lipase. Lipase can be used to efficiently catalyze the esterification of long-chain fatty acids with glycerol. The process of preparing diglyceride and glycerides of polyunsaturated fatty acid by lipase has been applied in practical production. Since butyric acid has different physical and chemical properties from medium and long-chain fatty acids, the catalytic activity of lipase is very low during the preparation of glyceryl butyrate using the existing enzymatic synthesis method for glyceride. When the reaction reaches equilibrium, the conversion rate of butyric acid is also very low. This may be due to the fact that existing lipases are available for interface activation, however, butyric acid and glycerol have good mutual solubility so that the esterification reaction system cannot provide an interface, which greatly reduces the catalytic activity of lipase. As for why the conversion rate of butyric acid is low when the reaction reaches equilibrium, there is no research to explain this phenomenon.

The present invention has found that the addition of ethyl acetate or ethyl formate as an additive in the lipase-catalyzed esterification reaction of butyric acid and glycerol can improve the catalytic efficiency of lipase and increase the conversion rate of butyric acid, thereby forming the method of this invention.

Compared with the prior art, the beneficial effects of the present invention are as follows:

(1) The present invention catalyzes the esterification reaction of n-butyric acid and glycerin at normal temperature and normal pressure with lipase, thereby reducing the energy consumption of the reaction and avoiding the use of the water-carrying agent;

(2) The addition of ethyl acetate and/or methyl acetate as an additive increases the catalytic efficiency of the lipase and the conversion rate of butyric acid.

DETAILED DESCRIPTION OF THE EMBODIMENTS

The embodiments of the invention are described in more detail below by the following examples. In the examples, all percentages are by mass. The content of butyric acid in the reaction product was determined by gas chromatography, and the conversion rate of butyric acid was calculated by the following formula:

conversion rate of butyric acid=(original amount of butyric acid−remaining amount of butyric acid)/original amount of butyric acid*100%

EXAMPLE 1

88 g of n-butyric acid, 92 g of glycerin, and 10 g of ethyl acetate were added to a reaction vessel, and after mixing, Lipozyme TL 100L lipase 1.0 g (purchased from Novozymes (China) Biotechnology Co., Ltd.) was added to start the esterification reaction. The temperature of the reaction was controlled at 40° C. and the stirring speed was 400 rpm. After 12 hours of continuous reaction, the esterification reaction reached equilibrium state. Then the stirring was stopped and the esterification was terminated. The resulted mixture was allowed to stand for 5 min for stratification, and the upper organic phase was recovered. The ethyl acetate in the organic phase was recovered by distillation under reduced pressure to obtain glyceryl butyrate. The conversion rate of butyric acid in the product was tested to be 90.1%, the content of glyceryl monobutyrate occupied 91.7% of the total glyceryl butyrate, and the content of glyceryl dibutyrate and glyceryl tributyrate was 8.3%.

EXAMPLE 2

176 g of n-butyric acid, 184 g of glycerin, and 100 g of ethyl formate were added to a reaction vessel, and after mixing, Lipozyme TL 100L lipase 3.0 g (purchased from Novozymes (China) Biotechnology Co., Ltd.) was added to start the esterification reaction. The temperature of the reaction was controlled at 40° C. and the stirring speed was 400 rpm. After 12 hours of continuous reaction, the esterification reaction reached equilibrium state. Then the stirring was stopped and the esterification was terminated. The resulted mixture was allowed to stand for 5 min for stratification, and the upper organic phase was recovered. The ethyl formate in the organic phase was recovered by distillation under reduced pressure to obtain glyceryl butyrate. The conversion rate of butyric acid in the product was tested to be 92.3%, the content of glyceryl monobutyrate occupied 87.9% of the total glyceryl butyrate, and the content of glyceryl dibutyrate and glyceryl tributyrate was 12.2%.

EXAMPLE 3

88 g of n-butyric acid, 46 g of glycerin, and 10 g of ethyl acetate were added to a reaction vessel, and after mixing, Lipozyme®CALB lipase 1.0 g (purchased from Novozymes (China) Biotechnology Co., Ltd.) was added to start the esterification reaction. The temperature of the reaction was controlled at 45° C. and the stirring speed was 400 rpm. After 12 hours of continuous reaction, the esterification reaction reached equilibrium state. Then the stirring was stopped and the esterification was terminated. The resulted mixture was allowed to stand for 5 min for stratification, and the upper organic phase was recovered. The ethyl acetate in the organic phase was recovered by distillation under reduced pressure to obtain glyceryl butyrate. The conversion rate of butyric acid in the product was tested to be 93.2%, the content of glyceryl monobutyrate occupied 51.6% of the total glyceryl butyrate, and the content of glyceryl dibutyrate and glyceryl tributyrate was 48.4%.

COMPARATIVE EXAMPLE 1

88 g of n-butyric acid and 92 g of glycerin were added to a reaction vessel, and after mixing, Lipozyme TL 100L lipase 1.0 g was added to start the esterification reaction. The temperature of the reaction was controlled at 40° C. and the stirring speed was 400 rpm. After 12 hours of continuous reaction, the stirring was stopped and the esterification was terminated. The resulted mixture was allowed to stand for 5 min for stratification, and the upper organic phase was recovered to obtain glyceryl butyrate. The conversion rate of butyric acid in the product was tested to be 7.4%, glyceryl monobutyrate contributed most to the total glyceryl butyrate.

COMPARATIVE EXAMPLE 2

88 g of n-butyric acid and 92 g of glycerin were added to a reaction vessel, and after mixing, Lipozyme®CALB lipase 1.0 g was added to start the esterification reaction. The temperature of the reaction was controlled at 45° C. and the stirring speed was 200 rpm. After 12 hours of continuous reaction, the esterification reaction reached equilibrium state. Then the stirring was stopped and the esterification was terminated. The resulted mixture was allowed to stand for 5 min for stratification, and the upper organic phase was recovered to obtain glyceryl butyrate. The content of glyceryl monobutyrate occupied 77.3% of the total glyceryl butyrate, and the content of glyceryl dibutyrate and glyceryl tributyrate was 22.7%.

The invention claimed is:

1. An enzymatic method for preparing glyceryl butyrate, comprising:
   (1) carrying out an esterification reaction between n-butyric acid and glycerol using lipase as a catalyst and ethyl acetate and/or ethyl formate as an additive;
   (2) separating the reaction product and recovering the additive by distillation under reduced pressure to obtain glyceryl butyrate.

2. The method according to claim 1, wherein the additive is added in an amount of 10%-60% by mass of the n-butyric acid.

3. The method according to claim 1, wherein the molar ratio of the n-butyric acid to the glycerol in step (1) is 3:1-1:3.

4. The method according to any of claim 1, wherein the lipase is added in an amount of 0.5%-10% by mass of the n-butyric acid.

5. The method according to claim 4, wherein the lipase in step (1) is selected from at least one of lipase of *Rhizopus, Aspergillus, Mucor*, bacteria and yeast, and pancreatic lipase.

6. The method according to claim 4, wherein the esterification reaction is carried out at 20° C.-50° C. with stirring at a speed of 200 rpm or more.

7. The method according to claim 4, wherein the separating in step (2) is natural stratification, then the organic phase is recovered, and ethyl acetate is distilled under reduced pressure to obtain glyceryl butyrate.

8. The method according to claim 2, wherein the lipase is added in an amount of 0.5%-10% by mass of the n-butyric acid.

9. The method according to claim 8, wherein the lipase in step (1) is selected from at least one of lipase of *Rhizopus, Aspergillus, Mucor*, bacteria and yeast, and pancreatic lipase.

10. The method according to claim 8, wherein the esterification reaction is carried out at 20° C.-50° C. with stiffing at a speed of 200 rpm or more.

11. The method according to claim 8, wherein the separating in step (2) is natural stratification, then the organic phase is recovered, and ethyl acetate is distilled under reduced pressure to obtain glyceryl butyrate.

12. The method according to claim 3, wherein the lipase is added in an amount of 0.5%-10% by mass of the n-butyric acid.

13. The method according to claim 12, wherein the lipase in step (1) is selected from at least one of lipase of *Rhizopus, Aspergillus, Mucor*, bacteria and yeast, and pancreatic lipase.

14. The method according to claim 12, wherein the esterification reaction is carried out at 20° C.-50° C. with stiffing at a speed of 200 rpm or more.

15. The method according to claim 12, wherein the separating in step (2) is natural stratification, then the organic phase is recovered, and ethyl acetate is distilled under reduced pressure to obtain glyceryl butyrate.

* * * * *